United States Patent
Smith

(10) Patent No.: US 6,859,137 B1
(45) Date of Patent: Feb. 22, 2005

(54) FLATWARE AND TABLEWARE WITH SIGNALING MEANS FOR USE BY VISUALLY IMPAIRED USERS

(76) Inventor: Earline Smith, 8507 S. Olive St., Los Angeles, CA (US) 90003

( * ) Notice: Subject to any disclaimer, the term of this patent is extended or adjusted under 35 U.S.C. 154(b) by 37 days.

(21) Appl. No.: 10/638,922

(22) Filed: Aug. 11, 2003

(51) Int. Cl.[7] .............................................. H04B 3/36
(52) U.S. Cl. ............................. 340/407.1; 340/573.1; 340/825.19; 116/204
(58) Field of Search ..................... 340/407.1, 573.1, 340/825.19; 200/308, 404; 116/204, 279

(56) References Cited

U.S. PATENT DOCUMENTS

| | | | |
|---|---|---|---|
| 4,765,465 A | | 8/1988 | Yamada et al. ............. 206/217 |
| 4,993,156 A | * | 2/1991 | Craven ........................ 30/142 |
| 5,005,711 A | | 4/1991 | Peatross et al. ............ 211/70.7 |
| 5,176,282 A | * | 1/1993 | Rapaz ........................ 220/574 |
| 5,251,758 A | * | 10/1993 | Kolacek ..................... 206/542 |
| 5,269,717 A | | 12/1993 | Tardif ......................... 446/71 |
| 5,638,981 A | | 6/1997 | Crane et al. ............. 220/574.1 |
| 5,649,654 A | * | 7/1997 | Hayward, Jr. ............... 224/270 |

* cited by examiner

Primary Examiner—Daniel Wu
Assistant Examiner—Travis Hunnings
(74) Attorney, Agent, or Firm—Goldstein Law Offices, P.C.

(57) ABSTRACT

Flatware and tableware having signaling means for aiding a visually impaired user in locating and retrieving food from the tableware using the flatware. A signaling means assembly is housed within the flatware handle, the assembly having a magnet and a spring. The tableware has a central food-receiving surface and a metal upper rim. Upon bringing the signaling means assembly of the flatware into close proximity with the tableware metal rim, a magnetic force is exchanged that pulls the magnet towards the tableware, compresses the spring, and serves as a guide to the user. After the flatware moves past the rim, the magnet oscillates upon the spring and causes the flatware to vibrate. The vibrations generates a humming sound that signals to the user that contact has been established.

4 Claims, 2 Drawing Sheets

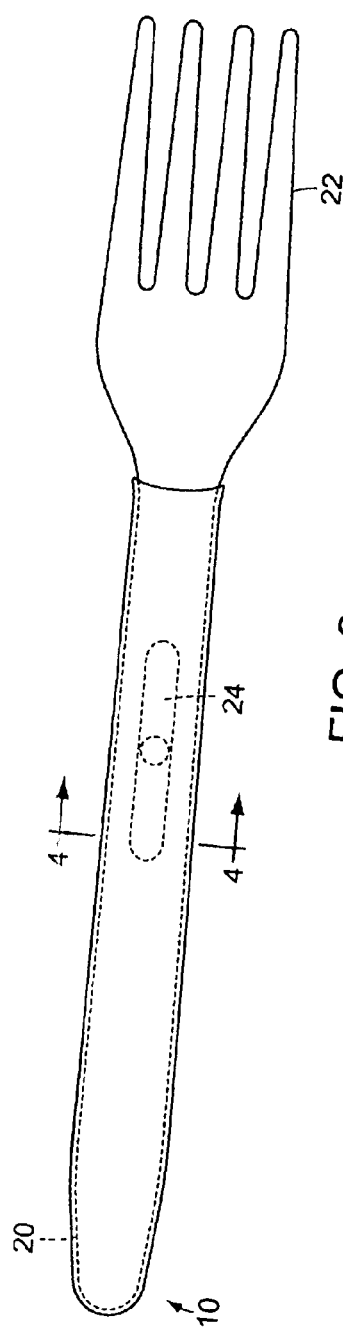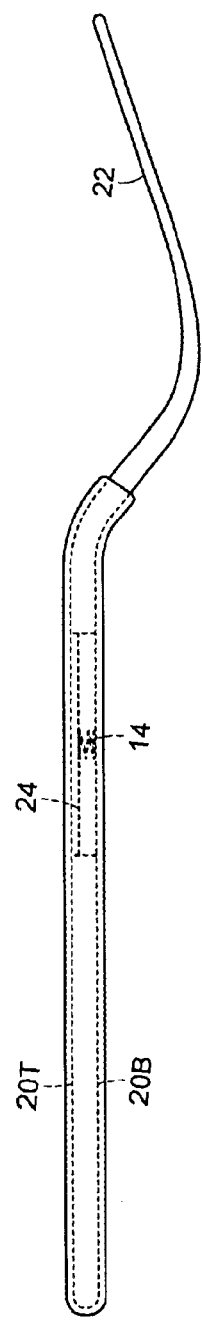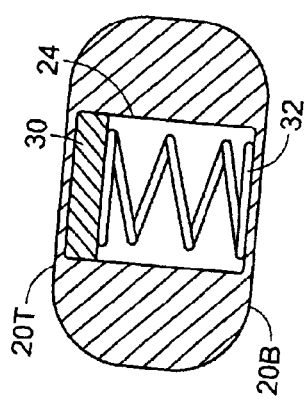
FIG. 2
FIG. 3
FIG. 4

FLATWARE AND TABLEWARE WITH SIGNALING MEANS FOR USE BY VISUALLY IMPAIRED USERS

BACKGROUND OF THE INVENTION

The invention relates to flatware and tableware with signaling means for use by visually impaired individuals. In particular, the invention is a set of eating utensils each having a magnet and a spring incorporated therein, said utensils used in conjunction with metal rimmed tableware. Upon bringing the utensil magnet into close proximity with the tableware metal rim, the spring vibrates causing a humming sound.

Blindness and vision impairment affect nearly 1.3 million people living in the United States, and approximately 50,000 new cases are reported every year. Whether a person is born blind or loses his/her vision over a course of time, the visually impaired person must learn how to perform simple everyday tasks, such as navigating around his or her home and community, dressing himself/herself, reading in Braille, and feeding himself/herself.

The task of eating a meal without another's aid can be daunting and arduous for a blind or visually impaired person. The person must learn to use a fork, knife, or spoon to locate and pick up pieces of food from a plate and then lift the utensil to his/her mouth. In order to aid in this process, food is typically arranged on a plate in a set manner so the person knows where to find different food groups on the plate. However, the difficult aspect of feeding oneself often lies in making contact between the plate and the eating utensil.

Thus, there exists a need for a set of flatware that is used in conjunction with specially constructed tableware to aid a visually impaired person in making contact between the flatware and tableware. The flatware is equipped with a signaling means assembly, and the tableware has a metal rim. Thus, as the flatware is brought into the vicinity of the tableware, the flatware signaling means assembly guides the flatware towards the tableware and upon contact, a humming sound is produced.

U.S. Pat. No. 5,638,981 to Crane et al. discloses tableware with utensil support. The tableware has a food-receiving surface formed with a hollowed out recess which is sized to receive the bowl of a spoon or fork therein.

U.S. Pat. No. 5,269,717 to Tardif discloses dishware having a liquid-filled rim and eating implements for use therewith.

U.S. Pat. No. 5,005,711 to Peatross et al. discloses a utensil holder apparatus for use by visually impaired individuals. The apparatus comprises a plurality of container, each with an appropriate utensil designation mounted vertically and orthogonally relative to an annular rim of the container.

U.S. Pat. No. 4,765,465 to Yamada et al. discloses eating utensils having a sound generating means. The utensil, such as a cup, has a sound generating circuit at the bottom to produce a melody when the cup is lifted up from a surface, such as a table.

While these units may be suitable for the particular purpose employed, or for general use, they would not be as suitable for the purposes of the present invention as disclosed hereafter.

SUMMARY OF THE INVENTION

In view of the foregoing disadvantages inherent in the prior art, the present invention provides improved flatware and tableware having signaling means for aiding a visually impaired person in locating and retrieving food with the flatware from the tableware. As such, the general purpose of the present invention, which will be described subsequently in greater detail, is to provide new and improved flatware and tableware having signaling means which has all the advantages of the prior art and none of the disadvantages.

To attain this, the present invention essentially comprises flatware and tableware having signaling means for aiding a visually impaired user in locating and retrieving food from the tableware using the flatware. A signaling means assembly is housed within the flatware handle, the assembly having a magnet and a spring. The tableware has a central food-receiving surface and a metal upper rim. Upon bringing the signaling means assembly of the flatware into close proximity with the tableware metal rim, a magnetic force is exchanged that pulls the magnet towards the tableware, compresses the spring, and serves as a guide to the user. After the flatware moves past the rim, the magnet oscillates upon the spring and causes the flatware to vibrate. The vibrations generates a humming sound that signals to the user that contact has been established.

It is an object of the invention to produce flatware and tableware that aids a visually impaired person in locating and retrieving food on the tableware unassisted. Accordingly, the flatware handle has a magnet incorporated therein and the tableware has a metal rim. Upon bringing the flatware handle into close proximity to the tableware metal rim, a magnetic force is exchanged that produces a gentle pull. This pull signals to the user that the flatware is positioned over the tableware.

It is a further object of the invention to produce flatware and tableware that produces a humming sound to signal to a visually impaired person that contact has been made between the flatware and the tableware. Accordingly, the flatware handle has a spring that extends upward from the magnet. Once the flatware handle is brought into contact with the tableware metal rim, the magnetic attraction causes the spring to gently vibrate and produce a humming sound.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 2 is a top plan view of the flatware, illustrating the handle hollow portion in broken lines, with the signaling means assembly housed therein.

FIG. 3 is a side elevational view of the flatware, illustrating the hollow portion of the handle in broken lines, with the spring and magnet housed therein.

FIG. 4 is a cross sectional view taken generally along line 4 in FIG. 2.

REFERENCE NUMERALS

Figure 1:
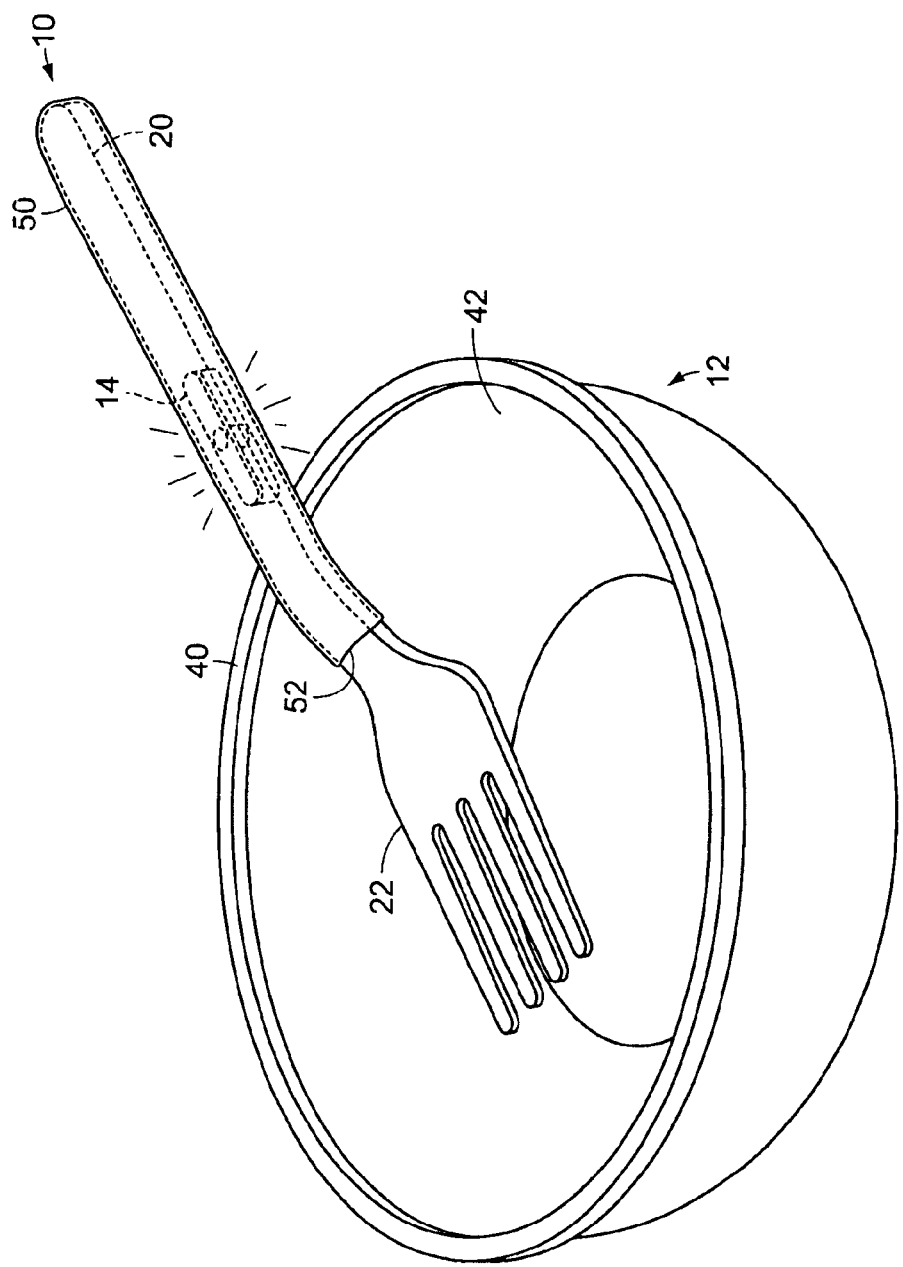
FIG. 1 is a diagrammatic perspective view of the flatware and tableware, illustrating the production of a humming sound upon contact between the flatware handle and the tableware metal rim.

10 flatware
12 tableware 14 signaling means assembly
20 handle
20T handle top surface
20B handle bottom surface
22 head
24 handle hollow portion
30 magnet
32 spring
40 tableware upper rim
42 tableware food-receiving surface
50 sleeve
52 sleeve opening.

DETAILED DESCRIPTION OF THE PREFERRED EMBODIMENTS

FIG. 1 illustrates flatware 10 and tableware 12 having signaling means for aiding a visually impaired user in locating and retrieving food from the tableware 12 using the flatware 10. While the figures illustrate the flatware 10 in the form of a fork and the tableware 12 in the form of a bowl, it should be noted that spoons, knives, plates, or other feasible forms of flatware and tableware may also be employed. The flatware 10 essentially is equipped with a signaling means assembly 14 that comprises a magnet 30 and a spring 32, and the tableware 12 has a metal rim 40, whereby upon bringing the signaling means assembly 14 of the flatware 10 into close proximity with the tableware metal rim 40, a magnetic force is exchanged and a humming sound is generated. This force serves as a guide to the user, signaling that the flatware 10 is in the immediate proximity of the tableware 12, and the humming sound signals to the user when contact is established between the flatware 10 and the tableware 12.

The flatware 10, in the form of a fork for illustrative purposes only, comprises a handle 20 and a head 22, the head 22 being in the form of prongs on a fork, a bowl on a spoon, or a cutting edge on a knife. The handle 20 extends outward from the head 22, said handle 20 used to hold and maneuver the flatware 10. The handle 20 has a top surface 20T and a bottom surface 20B, wherein when the flatware 10 is held by a user, the top surface 20T is oriented upward away from the tableware 12 and the bottom surface 20B is oriented downward towards the tableware 12. The handle 20 has a hollow portion 24 positioned between the top and bottom surfaces 20T, 20B for accommodating the signaling means assembly 14, as will be described in greater detail hereinafter.

Additionally, a sleeve 50 having an opening 52 may be stretched over the flatware handle 20. The opening 52 extends over the handle 20 up to the head 22. The sleeve 50 is preferably constructed from a thin plastic material. When in place over the handle 20, the sleeve 50 provides a comfortable grip for the user, without hindering the sound generating assembly 14.

The tableware 12, in the form of a bowl for illustrative purposes only, comprises an upper rim 40 and a central food-receiving surface 42, wherein the rim 40 extends therearound. The rim 40 is constructed from metal in order to be conducive to the flatware signaling means assembly 14.

The signaling means assembly 14 is housed within the flatware handle hollow portion 24. The assembly 14 comprises a magnet 30 and a spring 32. When the assembly 14 is brought close to the tableware metal rim 40, a magnetic force is exchanged between the flatware 10 and the tableware 12. This force produces a gentle pull that aids in guiding the user towards the tableware 12. The magnet 30 is positioned adjacent to the handle bottom surface 20B and the spring 32 extends upward from the magnet 30 to the handle top surface 20T, as illustrated in FIG. 3.

In use, food is placed on the tableware 12 and the user chooses a piece of flatware 10 with which to eat. As the flatware 10 is brought into close proximity to the tableware 12, specifically with the handle bottom surface 20B oriented towards the tableware rim 40, the metal rim 40 provides a gentle pull to the magnet 30 in the handle 20 and compresses the spring. This pull serves to guide the flatware 10 towards the tableware 12, signaling to the user that he/she is moving the flatware 10 in the correct direction. After the flatware moves past the rim 40, the magnet oscillates upon the spring and causes the flatware to gently vibrate. This vibration produces a humming sound that signals to the user that the flatware 10 is positioned on the tableware 12.

In conclusion, herein is presented flatware and tableware having signaling means for signaling to a visually impaired user when the flatware is positioned on the tableware, thereby aiding the user in retrieving food from the tableware with the flatware. The invention is illustrated by example in the drawing figures, and throughout the written description. It should be understood that numerous variations are possible, while adhering to the inventive concept. Such variations are contemplated as being a part of the present invention.

What is claimed is:

1. A system for aiding a visually impaired person in locating and retrieving food, comprising:

tableware, the tableware comprising a central food-receiving surface and an upper rim, whereby the upper rim is constructed from metal; and flatware, the flatware comprising a head, a handle having a top surface, a bottom surface, and a hollow portion positioned between the top and bottom surfaces, and a signaling means assembly housed within the handle hollow portion, the signaling means assembly comprising a magnet, the magnet positioned directly above the handle bottom surface, whereby when the flatware is brought into close proximity to the tableware upper rim, a magnetic force is exchanged between the metal rim and the magnet, pulling the magnet towards the tableware, in order to aid in guiding the user towards the tableware.

2. The system as recited in claim 1, wherein the signaling means assembly further comprises a spring, the spring extending upward from the magnet to the handle top surface, thus when the flatware handle comes into contact with the tableware metal rim, the magnetic attraction between the handle magnet and the tableware metal rim causes the spring to compress, and the flatware to vibrate, said vibration producing a humming sound that signals to the user that the flatware is positioned on the tableware.

3. The system as recited in claim 1, wherein the flatware further comprising a sleeve having a sleeve opening, whereby the flatware handle in inserted into the sleeve through the sleeve opening.

4. The system as recited in claim 3, wherein the flatware sleeve is constructed from a thin plastic material.

* * * * *